United States Patent [19]

Nakao et al.

[11] 4,001,312
[45] Jan. 4, 1977

[54] AMINOALCOHOLS

[75] Inventors: Masaru Nakao; Kikuo Sasajima, both of Toyonaka; Isamu Maruyama, Minoo; Shigenari Katayama, Takarazuka; Hisao Yamamoto, Nishinomiya, all of Japan

[73] Assignee: Sumitomo Chemical Company, Limited, Osaka, Japan

[22] Filed: Aug. 14, 1974

[21] Appl. No.: 497,389

Related U.S. Application Data

[63] Continuation-in-part of Ser. No. 203,002, Nov. 29, 1971, abandoned.

[30] Foreign Application Priority Data

Dec. 9, 1970 Japan .......................... 45-109767

[52] U.S. Cl. ...................... 260/501.18; 260/343.7; 260/558 R; 260/570.5 C; 260/570.6; 424/280; 424/316; 424/330

[51] Int. Cl.² ......................................... C07C 91/28

[58] Field of Search ................ 260/570.6, 570.5 C, 260/570.7, 501.18, 343.7

[56] References Cited

UNITED STATES PATENTS

| 3,225,096 | 12/1965 | Mills et al. ................. 260/570.6 X |
| 3,412,154 | 11/1968 | Fleming et al. ............... 260/570.5 |
| 3,457,270 | 7/1969 | Fleming et al. ............. 260/570.7 X |
| 3,462,444 | 8/1969 | Beckett et al. ............. 260/570.5 X |
| 3,855,294 | 10/1967 | Podeson et al. ............ 260/570.6 X |

*Primary Examiner*—Robert V. Hines
*Attorney, Agent, or Firm*—Stevens, Davis, Miller & Mosher

[57] ABSTRACT

Novel 4-amino-1-butanol derivatives having excellent depressant activity on central nervous system. A preferred compound of the disclosure is 4-[2-(2-alkoxyphenoxy)ethylamino]-1-(4-fluorophenyl)-1-butanol and its pharmaceutically acceptable salts.

4 Claims, No Drawings

AMINOALCOHOLS

This is a continuation-in-part of U.S. application Ser. No. 203,002 filed on Nov. 29, 1971 and now abandoned.

The present invention relates to novel aminoalcohols. More particularly, the invention pertains to novel 4-amino-1-butanol derivatives useful as therapeutic agents, especially as central nervous system depressants.

The compounds of the present invention are represented by the formula (I):

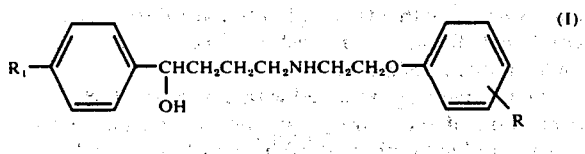

wherein
$R_1$ is halogen;
R is hydrogen or $C_1 - C_3$ alkoxy.

The pharmaceutically acceptable acid addition salts thereof are also a part of the present invention. The said salts include those prepared from both organic and inorganic acids such as, for example, hydrochloric, hydrobromic, sulfuric, phosphoric, nitric, acetic, fumaric, benzoic, tartaric, oxalic, citric, succinic, glycolic, salicylic, cinnamic, mandelic, ascorbic and sulfamic acids.

The compounds of the present invention can be prepared by the process illustrated in the following synthetic scheme:

The reaction is preferably carried out in the presence of a basic agent or condensing agent such as pyridine, triethylamine, sodium carbonate, sodium hydroxide, dicyclohexylcarbodiimide and the like.

The reaction is conveniently effected at a temperature between −20° C and about 80° C, and preferably at about room temperature or below, and the product can be isolated by usual procedure well known in the art.

The reduction, the second step of the process, is effected by treating the amidoketone (II) with a suitable reducing agent in a solvent inert under the conditions of the reaction. The reducing agents preferably employed include metal hydride complexes such as lithium aluminum hydride, diborane, sodium aluminum diethyl dihydride, a combination of sodium borohydride and aluminum chloride, a combination of sodium borohydride and boron trifluoride and the like. The preferred reaction solvents include diethyl ether, diisopropyl ether, tetrahydrofuran, dioxane, methylal, N-ethylmorphorine, ethylene glycol dimethyl ether, toluene and the like.

The reaction is preferably carried out at a temperature between about 0° C and 100° C, using a stoichiometric amount or more of the said reducing agent.

It is particularly preferred to use lithium aluminium hydride in refluxing ether, tetrahydrofuran, toluene or a mixture of the said solvents.

After the reaction is complete, the product can be isolated by a usual manner well known in the art, and optionally further purified by a well-known purification technique, e.g. recrystallization, and can, if desired, be converted to an acid addition salt thereof according to a conventional method.

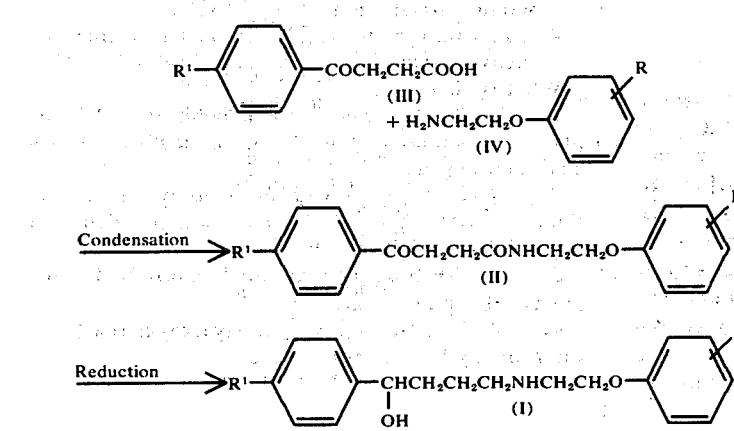

[In the formulae, R' and R are as defined above]

In the condensation, the first step of the process, a 3-benzoylpropionic acid of the formula (III) or its functionally active derivative is reacted with an amine of the formula (IV) in a suitable solvent. The said functionally active derivatives of the benzoylpropionic acid include chloride, bromide, anhydride, mixed anhydrides, p-nitrophenyl ester and the like. The said mixed anhydrides include those prepared from ethyl chloroformate, isobutyl chloroformate and the like.

The reaction solvent preferably employed is a solvent which is inert under the conditions of the reaction and selected from the group consisting of ether, tetrahydrofuran, toluene, chloroform, acetone, ethyl acetate, dimethylformamide and the like.

The pharmacological evaluation of the compounds of the formula (I) demonstrated that they possessed a variety of depressant actions on the central nervous system. The compounds of the invention are effective in anti-apomorphine test and test for suppression of conditioned avoidance response in rats. They also possess anti-methamphetamine and psychomotor depressant effects. In view of these properties, the compounds according to the present invention are useful as a psychotropic agent.

The compounds according to the invention may be brought into a form suitable for administration according to a method known in the art. For the preparation of pharmaceutical compositions, they may be mixed with conventional diluent or carrier, and the resulting mixture or solution may be processed in usual manners to pharmaceutical dosage unit forms, for example, capsules, tablets, powders, pills, ampoules and the like.

The present invention will be further illustrated with reference to the following examples.

EXAMPLE 1

To a stirred solution of 10.4 g of 3-(4-fluorobenzoyl)-propionic acid and 6.0 g of triethylamine in 120 ml of tetrahydrofuran was added dropwise 6.0 g of ethyl chloroformate at a temperature below −5° C. After stirring was continued for half an hour, to the mixture was added a solution of 9.6 g of 2-(2-ethoxyphenoxy)ethylamine in 10 ml of tetrahydrofuran. Further stirring was continued at room temperature for 4 hours. The reaction mixture was filtered and the filtrate was concentrated to a residue under reduced pressure. 11 Grams of residual N-[2-(2-ethoxyphenoxy)-ethyl]-3-(4-fluorobenzoyl)propionamide was added in several portions to a stirring mixture of 3.6 g of lithium aluminum hydride and 130 ml of tetrahydrofuran. The resulting mixture was heated to 65° C and refluxed for 3 hours. To the cooled reaction mixture was added dropwise a solution of 20 ml of water and 60 ml of tetrahydrofuran.

After standing for 30 minutes, the whole was filtered, washed with 60 ml of tetrahydrofuran and the combined filtrate and washings were concentrated under reduced pressure.

The residue was extracted with 200 ml of ether. Concentration of the extract gave 4-[2-(2-ethoxyphenoxy)ethylamino]-1-(4-fluorophenyl)-1-butanol.

EXAMPLE 2

1st Step

To a stirred solution of 10.4 g of 3-(4-fluorobenzoyl)-propionic acid and 6.0 g of triethylamine in 120 ml of tetrahydrofuran was added dropwise 6.0 g of ethyl chloroformate at a temperature below 0° C. After stirring was continued for half an hour, to the mixture was added a solution of 9.6 g of 2-(2-ethoxyphenoxy)ethylamine in 10 ml of tetrahydrofuran. Further stirring was continued at room temperature for 4 hours. The reaction mixture was filtered and the filtrate was concentrated to a residue under reduced pressure. The residue was recrystallized from benzene-hexane to give N-[2-(2-ethoxyphenoxy)ethyl]-3-(4-fluorobenzoyl)-propionamide melting at 98° – 100° C.

2nd Step

To a stirred mixture of 3.6 g of lithium aluminum hydride, 40 ml of ether and 100 ml of tetrahydrofuran was added in several portions 10 g of the above-obtained amide at about room temperature. The mixture was stirred under reflux for 2 hours and cooled. To the cooled reaction mixture was added dropwise a solution of 20 ml of water and 60 ml of tetrahydrofuran.

After standing for 30 minutes, the whole was filtered, and washed with 60 ml of tetrahydrofuran and the combined filtrate and washings were concentrated under reduced pressure.

The residue was extracted with 200 ml of ether. Concentration of the extract gave an oily residue, which was treated with ethereal oxalic acid to deposit a crystalline solid. Recrystallization of the resulting solid from ethanol gave 4-[2-(2-ethoxyphenoxy)ethylamino]-1-(4-fluorophenyl)-1-butanol oxalate melting at 127° – 128° C.

By a procedure similar to that as described above, the following compounds were obtained.

4-[2-(2-Methoxyphenoxy)ethylamino]-1-(4-fluorophenyl)-1-butanol oxalate, m.p. 144° – 145° C 4-[2-(2-n-Propoxyphenoxy)ethylamino]-1-(4-fluorophenyl)-1-butanol oxalate, m.p. 124° – 125° C 4-[2-(2-Isopropoxyphenoxy)ethylamino]-1-(4-fluorophenyl)-1-butanol oxalate, m.p. 112° – 115° C 4-(2-Phenoxyethyl)amino-1-(4-fluorophenyl)-1-butanol oxalate, m.p. 161° – 162° C 4-[2-(2-Ethoxyphenoxy)ethylamino]-1-(4-chlorophenyl)-1-butanol oxalate, m.p. 114° – 117° C.

What is claimed is:
1. 4-[2-(2-Ethoxyphenoxy)ethylamino]-1-(4-fluorophenyl)-1-butanol and its pharmaceutically acceptable acid addition salt.
2. 4-[2-(2-Isopropoxyphenoxy)ethylamino]-1-(4-fluorophenyl)-1-butanol and its pharmaceutically acceptable acid addition salt.
3. 4-[2-(2-Ethoxyphenoxy)ethylamino]-1-(4-fluorophenyl)-1-butanol oxalate.
4. 4-[2-(2-Isopropoxyphenoxy)ethylamino]-1-(4-fluorophenyl)-1-butanol oxalate.

* * * * *